US012268427B2

United States Patent
Morris

(10) Patent No.: US 12,268,427 B2
(45) Date of Patent: Apr. 8, 2025

(54) SELF-DRILLING BONE CEMENT DELIVERY CANNULA AND METHODS FOR USE

(71) Applicant: Bone Solutions, Inc., Colleyville, TX (US)

(72) Inventor: Frankie L. Morris, Colleyville, TX (US)

(73) Assignee: Bone Solutions, Inc., Colleyville, TX (US)

( * ) Notice: Subject to any disclaimer, the term of this patent is extended or adjusted under 35 U.S.C. 154(b) by 339 days.

(21) Appl. No.: 17/818,753

(22) Filed: Aug. 10, 2022

(65) Prior Publication Data

US 2023/0149062 A1 May 18, 2023

Related U.S. Application Data

(60) Provisional application No. 63/231,869, filed on Aug. 11, 2021.

(51) Int. Cl.
*A61B 17/88* (2006.01)
*A61B 17/16* (2006.01)
*A61B 17/34* (2006.01)
*A61B 17/00* (2006.01)
*A61B 17/56* (2006.01)

(52) U.S. Cl.
CPC ...... *A61B 17/8805* (2013.01); *A61B 17/1637* (2013.01); *A61B 17/3472* (2013.01); *A61B 17/8811* (2013.01); *A61B 17/8819* (2013.01); *A61B 17/8833* (2013.01); *A61B 2017/00477* (2013.01); *A61B 2017/347* (2013.01); *A61B 2017/564* (2013.01)

(58) Field of Classification Search
CPC ......... A61B 2017/00477; A61B 17/16; A61B 17/1637; A61B 17/8802; A61B 17/8805; A61B 17/8811; A61B 17/8819; A61B 17/8833; A61B 2017/347; A61B 17/3472
See application file for complete search history.

(56) References Cited

U.S. PATENT DOCUMENTS

| 4,813,808 A * | 3/1989 | Gehrke .................. F16D 3/224 403/372 |
| 7,927,339 B2 | 4/2011 | Ralph |
| 8,574,303 B2 | 11/2013 | Sharkey |

(Continued)

FOREIGN PATENT DOCUMENTS

JP 2003024339 A * 1/2003 ......... A61B 17/8819

*Primary Examiner* — Larry E Waggle, Jr.
(74) *Attorney, Agent, or Firm* — McDonnell Boehnen Hulbert & Berghoff LLP

(57) ABSTRACT

The present disclosure relates to a device including an elongated hollow shaft having a proximal end and a distal end. The device also includes a first attachment mechanism coupled to the proximal end of the elongated hollow shaft. The device also includes a rod having a proximal end and a distal end. The rod is removably positioned at least partially within a lumen of the elongated hollow shaft. The device also includes a second attachment mechanism coupled to the rod between the proximal end of the rod and the distal end of the rod. The first attachment mechanism and the second attachment mechanism are configured to be removably coupled to one another. The device also includes a cap configured to be removably coupled to the second attachment mechanism.

16 Claims, 6 Drawing Sheets

(56) References Cited

U.S. PATENT DOCUMENTS

| | | | | |
|---|---|---|---|---|
| 8,986,312 B2* | 3/2015 | Georgy | ............. | A61B 17/8833 |
| | | | | 606/92 |
| 9,681,889 B1* | 6/2017 | Greenhalgh | ....... | A61B 17/3421 |
| 9,974,549 B2 | 5/2018 | Lele | | |
| 10,064,671 B2* | 9/2018 | Sharkey | ............. | A61B 17/8811 |
| 11,246,637 B2* | 2/2022 | Lee | ................... | A61B 17/8897 |
| 11,478,231 B2* | 10/2022 | McGillicuddy | ...... | A61B 10/025 |
| 2007/0010843 A1* | 1/2007 | Green | ................ | A61B 17/3421 |
| | | | | 606/167 |
| 2011/0125157 A1 | 5/2011 | Sharkey | | |

* cited by examiner

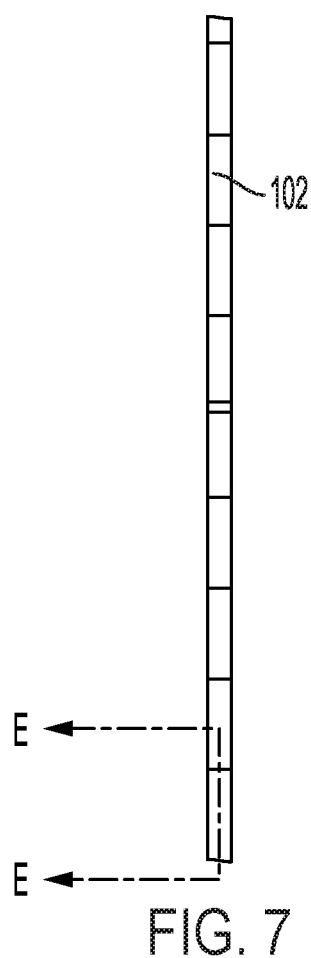
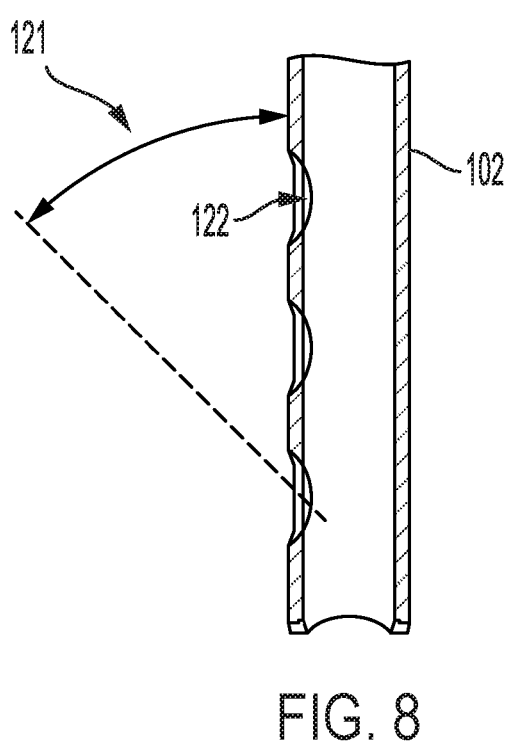
FIG. 7
FIG. 8

SELF-DRILLING BONE CEMENT DELIVERY CANNULA AND METHODS FOR USE

RELATED APPLICATIONS

This application claims priority to U.S. Provisional Application No. 63/231,869 entitled "Self-Drilling Bone Cement Delivery Cannula and Methods for Use," filed on Aug. 11, 2021, the contents of which are hereby incorporated by reference in its entirety.

TECHNICAL FIELD

The present disclosure relates to delivery cannula for use in surgery, particularly in orthopedic applications with bone voids.

BACKGROUND

Unless otherwise indicated herein, the materials described in this section are not admitted to be prior art to the claims in this application.

Many orthopedic medical procedures and treatments for require external and internal bone access to treat bone voids, bone lesions, and bone cysts. A cannula is one way to provide access to these bone voids, bone lesions, and bone cysts. Traditionally, a cannula is placed with trocar and cannula by pushing or hammering into place. The trocar is then removed and the pathway is generated. Problems arise when the cannula is not placed properly via hand or drill. Excessive hand or drilling only can lead to short placement, (i.e. not in the void) or far placement (i.e. past the void). Both of these situations can lead to improper treatment of the void space in the bone.

With these problems in mind, it is necessary to provide an instrument that can be placed by hand and or drilled into place directly into the patient's body. It is also necessary to having both cutting options within a single instrument can provide better control, better placement and better outcomes for the surgeon and patients overall health.

SUMMARY

In view of the foregoing, the present disclosure provides a device and corresponding method for accessing a treatment area of a bone in a patient. The device is configured to access bone voids within a bone and inject materials into that void. The device will be able to access the void by hand or can be power by a drill. Once in place an autograft, allograft or synthetic bone void graft cement can be injected into the void via the device.

Thus, in a first aspect, the present disclosure provides a device including an elongated hollow shaft having a proximal end and a distal end. The device also includes a first attachment mechanism coupled to the proximal end of the elongated hollow shaft. The device also includes a rod having a proximal end and a distal end. The rod is removably positioned at least partially within a lumen of the elongated hollow shaft. The device also includes a second attachment mechanism coupled to the rod between the proximal end of the rod and the distal end of the rod. The first attachment mechanism and the second attachment mechanism are configured to be removably coupled to one another. The device also includes a cap configured to be removably coupled to the second attachment mechanism.

In a second aspect, the present invention provides a method for accessing a treatment area in a bone, the method comprising: (i) providing the device of the first aspect, (ii) inserting the distal end of the rod and the distal end of the elongated hollow shaft into the treatment area of the bone, (iii) decoupling the first attachment mechanism from the second attachment mechanism, (iv) removing the rod and the second attachment mechanism from the device, (v) injecting a reabsorbable bio-material composition through the lumen of the elongated hollow shaft and into the treatment area in the bone, and (iv) removing the elongated hollow shaft from the treatment area in the bone.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7 illustrates a side view of the elongated hollow shaft of FIG. 1, according to an exemplary embodiment.

FIG. 8 illustrates a side cross-section view of the distal end of the elongated hollow shaft along line E-E of FIG. 7, according to an exemplary embodiment.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The exemplary embodiments described herein are not meant to be limiting. It will be readily understood that the aspects of the present disclosure, as generally described herein and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, "distal" with respect to a portion of the apparatus means the end of the device (when in use) nearer the treatment zone (e.g., the treatment area in a bone) of the subject and the term "proximal" means the portion of the device (when in use) further away from the treatment zone of the subject and nearer the access site and the operator.

As used herein, with respect to measurements and angles, "about" means +/−5%.

The present disclosure provides a device and corresponding method for accessing a treatment area of a bone in a patient. The device is configured to access bone voids within a bone and inject materials into that void. The device will be able to access the void by hand or can be power by a drill. Once in place, an autograft, allograft, or synthetic bone void graft cement can be injected into the void via the device. Additional use cases are contemplated as well.

Figure 1:
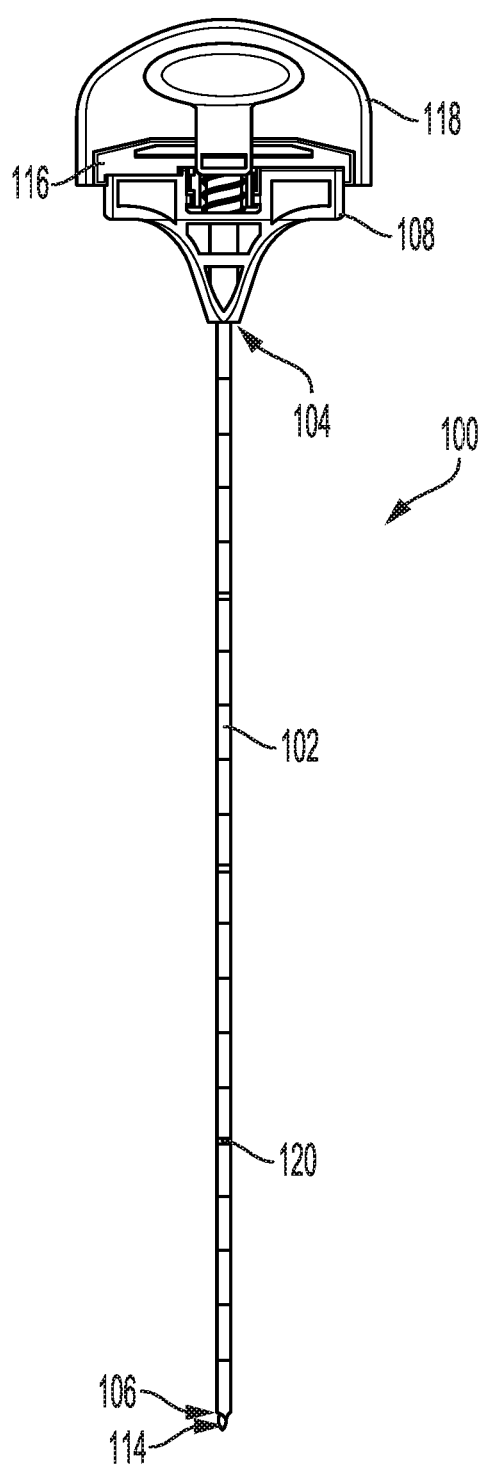
FIG. 1 illustrates a side view of a device, according to an exemplary embodiment.
Figure 2:
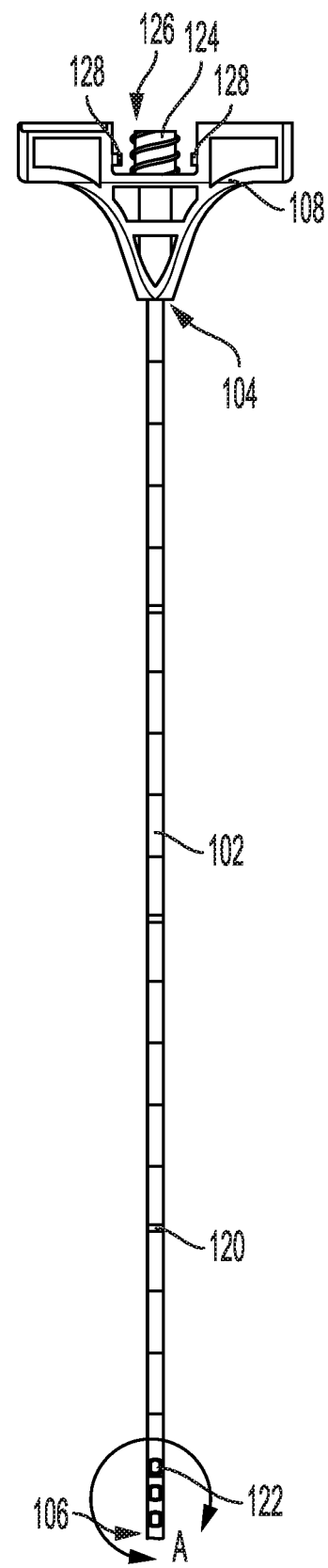
FIG. 2 illustrates a side view of the elongated hollow shaft and the first attachment mechanism of the device of FIG. 1, according to an exemplary embodiment.

With reference to the Figures, the present disclosure provides a device 100 for accessing a treatment area of a bone in a patient. FIG. 1 illustrates a side view of the device 100. The device 100 includes an elongated hollow shaft 102 having a proximal end 104 and a distal end 106. The device 100 also includes a first attachment mechanism 108 coupled to the proximal end 104 of the elongated hollow shaft 102. In one example, the first attachment mechanism 108 is permanently coupled to the proximal end 104 of the elongated hollow shaft 102. The combined elongated hollow shaft 102 and first attachment mechanism 108 is shown in FIG. 2.

Figure 3:
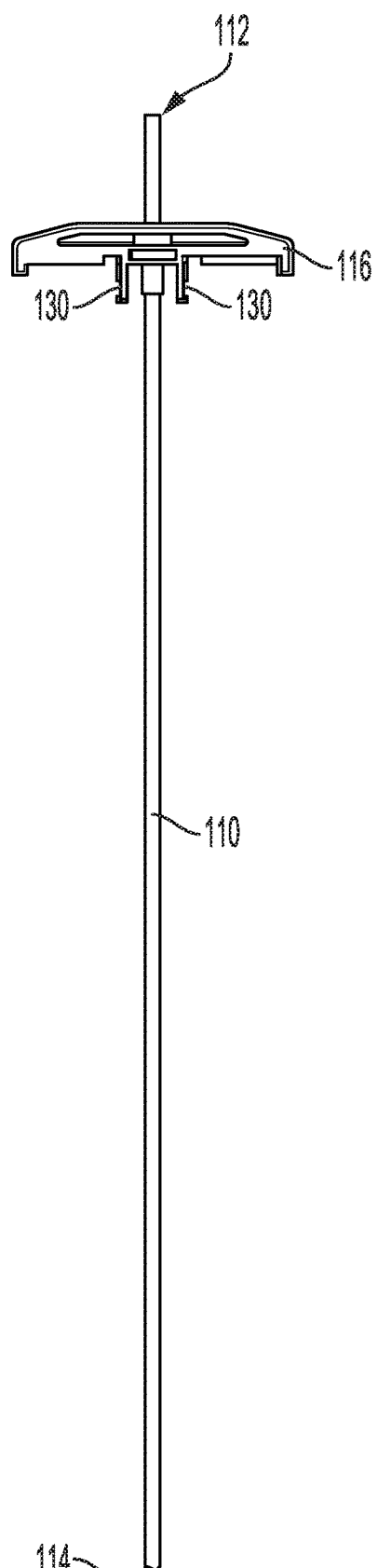
FIG. 3 illustrates a side view of the rod and the second attachment mechanism of the device of FIG. 1, according to an exemplary embodiment.
Figure 4:
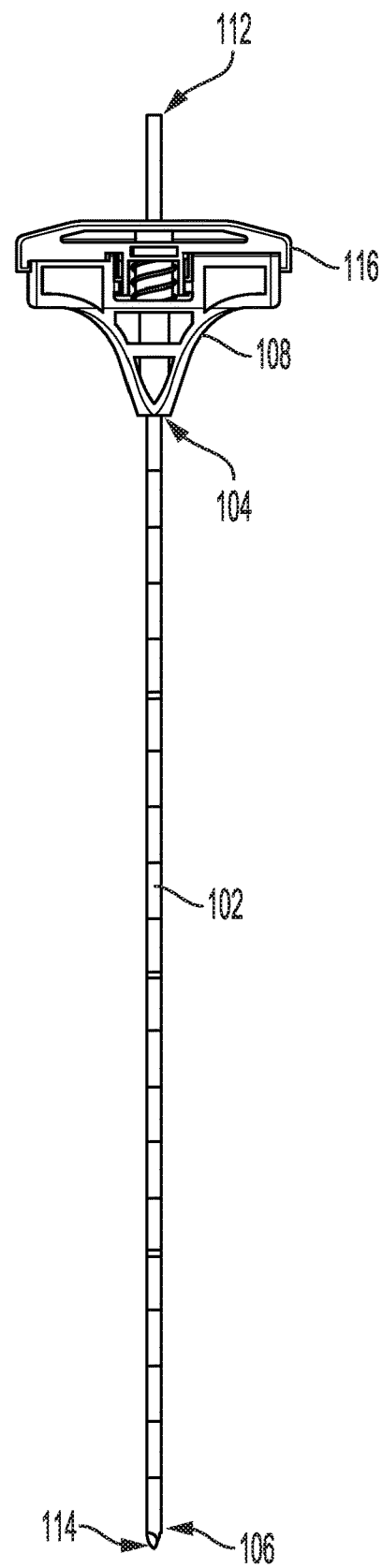
FIG. 4 illustrates a side view of the first attachment mechanism removably coupled to the second attachment mechanism of FIG. 1, according to an exemplary embodiment.

As shown in FIG. 1, the device 100 also includes a rod 110 having a proximal end 112 and a distal end 114. The rod 110 is configured to be removably positioned at least partially within a lumen of the elongated hollow shaft 102. The device 100 also includes a second attachment mechanism 116 coupled to the rod 110 between the proximal end 112 of the rod 110 and the distal end 114 of the rod 110. In one example, the second attachment mechanism 116 is permanently coupled to the rod 110. The combined the second attachment mechanism 116 and rod 110 is shown in FIG. 3. As shown in FIG. 3, the proximal end 112 of the rod 110 extends proximal to the second attachment mechanism 116. Such an arrangement enables the proximal end 112 of the rod 110 to be used as a drill bit to be inserted in a chuck of a drill, as discuss in additional detail below. As shown in FIG. 4, the first attachment mechanism 108 and the second attachment mechanism 116 are configured to be removably coupled to one another. As shown in FIGS. 1 and 4, when the first attachment mechanism 108 is removably coupled to the second attachment mechanism 116, the distal end 114 of the rod 110 extends distal to the distal end 106 of the elongated hollow shaft 102. Further, as shown in FIG. 1, the device 100 further includes a cap 118 configured to be removably coupled to the second attachment mechanism 116. In one example, as shown in FIG. 1, the cap 118 is configured to completely cover the proximal end 112 of the rod 110 when the cap 118 is coupled to the second attachment mechanism 116. The cap 118 can be removed from the second attachment mechanism 116 independently, resulting in the configuration shown in FIG. 4.

In one example, the distal end 114 of the rod 110 comprises a drill tip. In such an example, the proximal end 112 of the rod 110 may be coupled to a drill as discussed above to drive the distal end 114 of the rod 110 into the treatment area of the bone. In another example, the distal end 114 of the rod 110 comprises a sharp tip. In such an example, the distal end 114 of the rod 110 may be positioned into the treatment area of the bone via impaction.

As shown in FIG. 1, in one example an exterior surface of the elongated hollow shaft 102 includes a plurality of distance markings 120. Such distance markings 120 may be used to ensure that the device 100 is positioned in the proper location in the bone. In particular, fluoroscopy may be used to determine the location of the treatment area of the bone, and the distance markings 120 may be used to confirm that the device 100 is positioned at the appropriate depth in the treatment area of the bone.

In one example, as shown in FIGS. 5-10, the distal end 106 of the elongated hollow shaft 102 includes a plurality of side ports 122. In use, once the device 100 is positioned at the appropriate depth in the treatment area of the bone, the second attachment mechanism 116 is decoupled from the first attachment mechanism 108 and the rod 110 is removed from the lumen of the elongated hollow shaft 102. A reabsorbable bio-material composition is then injected through the lumen of the elongated hollow shaft and into the treatment area in the bone. The reabsorbable bio-material composition exits the plurality of side ports 122 to better spread the reabsorbable bio-material composition to the entirety of the treatment area of the bone. In one example, the first attachment mechanism includes a threaded component 124, and a syringe including the reabsorbable bio-material composition is configured to be removably coupled to the first attachment mechanism 108 via the threaded component 124.

Figures 5, 6:
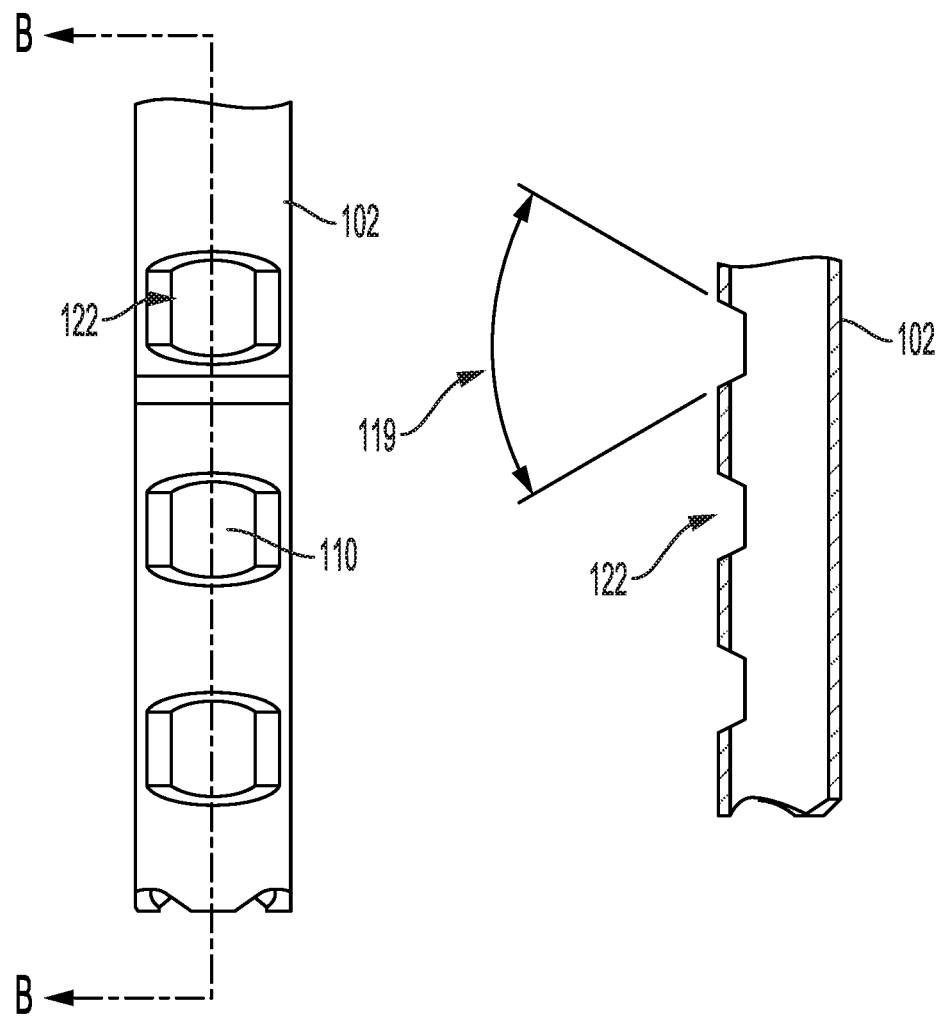
FIG. 5 illustrates a side view of the distal end of the elongated hollow shaft of FIG. 1, according to an exemplary embodiment.
FIG. 6 illustrates a side cross-section view of the distal end of the elongated hollow shaft along line B-B of FIG. 5, according to an exemplary embodiment.
Figure 9:
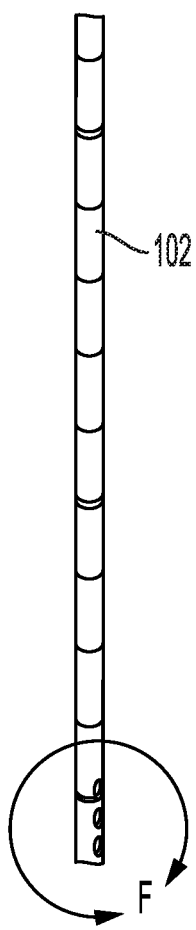
FIG. 9 illustrates a side view of the elongated hollow shaft of FIG. 1, according to an exemplary embodiment.
Figure 10:
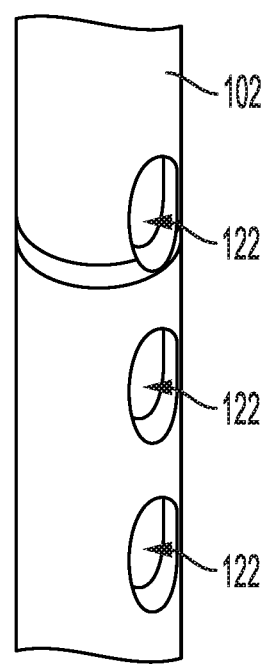
FIG. 10 illustrates a detailed view of the distal end of the elongated hollow shaft of FIG. 9, according to an exemplary embodiment.

The plurality of side ports 122 may take a variety of forms. In one example, as shown in FIGS. 5-6, the plurality of side ports 122 comprise angled cutouts. In one particular example, the angle 119 of the angled cutout is about 60 degrees. In another example, the angle 119 of the angled cutout is between about 30 degrees and about 70 degrees. In another example, as shown in FIGS. 7-8, the plurality of side ports 122 comprise angled circular cutouts. In one particular example, the angle 121 of the circular cutout with respect to the exterior surface of the elongated hollow shaft 102 is about 45 degrees. In one particular example, the angle 121 of the circular cutout with respect to the exterior surface of the elongated hollow shaft 102 is between about 30 degrees and about 60 degrees. In another example, as shown in FIGS. 9-10, the plurality of side ports 122 comprise straight circular cutouts with sidewalls that are perpendicular to the longitudinal axis of the elongated hollow shaft 102. Other arrangements of the plurality of side ports 122 are possible as well.

Figure 11:
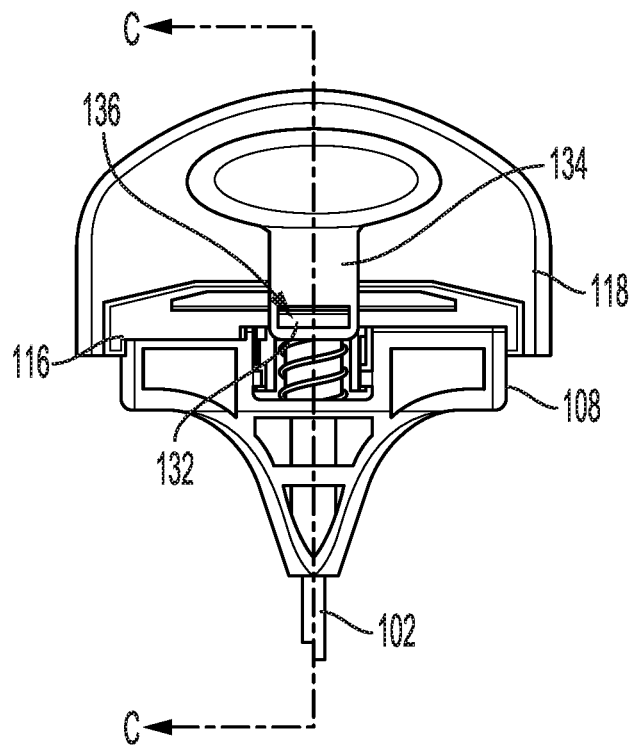
FIG. 11 illustrates a detailed view of the proximal end of the device of FIG. 1, according to an exemplary embodiment.

The first attachment mechanism 108 and the second attachment mechanism 116 may take a variety of forms. In one example, the first attachment mechanism 108 comprises an integral lock that is activated by a twisting motion between the first attachment mechanism 108 and the second attachment mechanism 116. In another example, as shown in FIG. 11, the first attachment mechanism 108 includes a cavity 126 including a pair of protrusions 128 directed inward from the cavity 126, and the second attachment mechanism 116 includes a pair of flexible arms 130. The pair of flexible arms 130 are configured to bend inward as the rod 110 is moved distally within the lumen of the elongated hollow shaft 102 and then snap around the pair of protrusions 128 to thereby removably couple the first attachment mechanism 108 to the second attachment mechanism 116. To decouple the first attachment mechanism 108 from the second attachment mechanism 116, the second attachment mechanism 116 is rotated with respect to the first attachment mechanism 108 until the pair of protrusions 128 no longer engage the pair of flexible arms 130.

Figure 12:
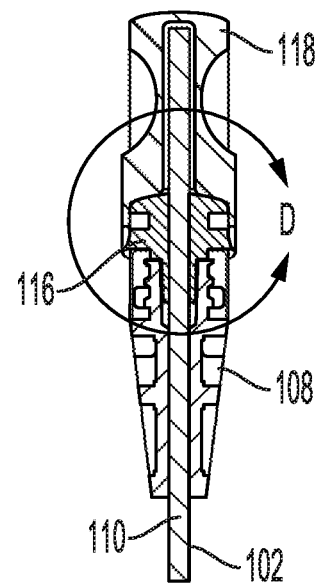
FIG. 12 illustrates a side cross-sectional view of the proximal end of the device along line E-E of FIG. 11, according to an exemplary embodiment.
Figure 13:
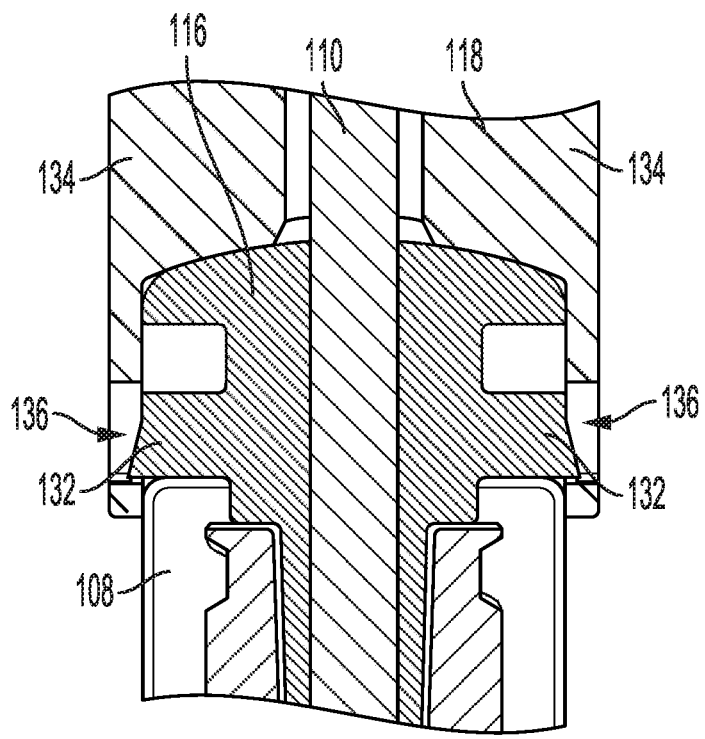
FIG. 13 illustrates a detailed view of the side cross-sectional view of the proximal end of the device of FIG. 12, according to an exemplary embodiment.

The cap 118 may be removably coupled to the second attachment mechanism 116 in a variety of ways. In one example, as shown in FIGS. 11-13, the second attachment mechanism 116 includes a pair of protrusions 132 directed outward, and the cap 118 includes a pair of flexible arms 134 including cutouts 136. The pair of flexible arms 134 are configured to bend outward as the cap 118 is moved distally with respect to the second attachment mechanism 116, and the cutouts 136 of the pair of flexible arms 134 are configured to snap around the pair of protrusions 132 to thereby removably couple the cap 118 to the second attachment mechanism 116. To decouple the cap 118 from the second attachment mechanism 116, the pair of flexible arms 134 are bent outward and the cap is moved in a proximal direction until the cutouts 136 of the pair of flexible arms 134 no longer engage the protrusions 132.

In operation, the present invention provides a method for accessing a treatment area in a bone, the method comprising: (i) providing the device of the first aspect, (ii) inserting the distal end of the rod and the distal end of the elongated hollow shaft into the treatment area of the bone, (iii) decoupling the first attachment mechanism from the second attachment mechanism, (iv) removing the rod and the second attachment mechanism from the device, (v) injecting a reabsorbable bio-material composition through the lumen of the elongated hollow shaft and into the treatment area in the bone, and (iv) removing the elongated hollow shaft from the treatment area in the bone.

Such a reabsorbable bio-material composition may be osteoconductive and osteoinductive, thereby enabling new bone growth in the treatment area in the bone. In such an example, the reabsorbable bio-material composition turns to bone to provide bone structure in the bone.

In one example, the method further includes rotating the elongated hollow shaft while injecting the reabsorbable bio-material composition.

In another example, the treatment area in the bone comprises one of a bone cyst, a bone marrow lesion, or a bone void. A bone cyst is a fluid-filled hole that develops inside a bone. Bone cysts do not usually cause any symptoms, they are not cancerous and they do not usually pose a serious threat to health. Bone marrow lesions (BMLs) or using older terminology "bone marrow edema" is characterized by excessive water signals in the marrow space on magnetic resonance imaging or ultrasound; BMLs constitute a central component of a wide variety of inflammatory and non-inflammatory rheumatologic conditions affecting the musculoskeletal system: BMLs are not only considered significant sources of pain but also linked to increased disease activity in many musculoskeletal conditions (for example, osteoarthritis, rheumatoid arthritis). The bone defects of the above method may be defects of the extremities and/or pelvic bone, as specific examples.

In another example, the method further includes removably coupling the first attachment mechanism to the second attachment mechanism, and removably coupling the cap to the second attachment mechanism prior to inserting the distal end of the rod and the distal end of the elongated hollow shaft into the treatment area of the bone. In one such example, inserting the distal end of the rod and the distal end of the elongated hollow shaft into the treatment area of the bone comprises manually rotating, via the cap, the distal end of the rod until the distal end of the rod reaches the treatment area in the bone.

In another example, the method further includes removably coupling the first attachment mechanism to the second attachment mechanism prior to inserting the distal end of the rod and the distal end of the elongated hollow shaft into the treatment area of the bone. In one such example, inserting the distal end of the rod and the distal end of the elongated hollow shaft into the treatment area of the bone comprises: coupling a drill to the proximal end of the rod, and rotating, via the drill, the rod until the distal end of the rod reaches the treatment area in the bone.

In another example of the method, injecting the reabsorbable bio-material composition through the lumen of the elongated hollow shaft and into the treatment area in the bone comprises: removably coupling a syringe including the reabsorbable bio-material composition to the first attachment mechanism, and injecting the reabsorbable bio-material composition via the syringe and through the lumen of the elongated hollow shaft and into the treatment area in the bone.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Because many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

What is claimed is:

1. A method for accessing a treatment area in a bone via a device, wherein the device comprises (i) an elongated hollow shaft having a proximal end and a distal end, (ii) a first attachment mechanism coupled to the proximal end of the elongated hollow shaft, (iii) a rod having a proximal end and a distal end, wherein the rod is removably positioned at least partially within a lumen of the elongated hollow shaft, (iv) a second attachment mechanism coupled to the rod between the proximal end of the rod and the distal end of the rod, wherein the first attachment mechanism and the second attachment mechanism are configured to be removably coupled to one another, and (v) a cap configured to be removably coupled to the second attachment mechanism, the method comprising:

(i) removably coupling the first attachment mechanism to the second attachment mechanism;

(ii) inserting the distal end of the rod and the distal end of the elongated hollow shaft into the treatment area of the bone by (a) coupling a drill to the proximal end of the rod, and (b) rotating, via the drill, the rod until the distal end of the rod reaches the treatment area in the bone;

(iii) decoupling the first attachment mechanism from the second attachment mechanism;

(iv) removing the rod and the second attachment mechanism from the device;

(v) injecting a reabsorbable bio-material composition through the lumen of the elongated hollow shaft and into the treatment area in the bone; and (vi) removing the elongated hollow shaft from the treatment area in the bone.

2. The method of claim 1, wherein the reabsorbable bio-material composition is osteoconductive and osteoinductive, thereby enabling new bone growth in the treatment area in the bone.

3. The method of any claim 1, wherein the reabsorbable bio-material composition turns to bone to provide bone structure in the bone.

4. The method of claim 1, further comprising:
rotating the elongated hollow shaft while injecting the reabsorbable bio-material composition.

5. The method of claim 1, wherein the treatment area in the bone comprises one of a bone cyst, a bone marrow lesion, or a bone void.

6. The method of claim 1, further comprising:
removably coupling the first attachment mechanism to the second attachment mechanism, and removably coupling the cap to the second attachment mechanism prior to inserting the distal end of the rod and the distal end of the elongated hollow shaft into the treatment area of the bone.

7. The method of claim 1, wherein injecting the reabsorbable bio-material composition through the lumen of the elongated hollow shaft and into the treatment area in the bone comprises:
removably coupling a syringe including the reabsorbable bio-material composition to the first attachment mechanism; and
injecting the reabsorbable bio-material composition via the syringe and through the lumen of the elongated hollow shaft and into the treatment area in the bone.

8. The method of claim 1, wherein the cap is configured to completely cover the proximal end of the rod when the cap is coupled to the second attachment mechanism.

9. The method of claim 1, wherein the distal end of the rod comprises one of a drill tip or a sharp tip.

10. The method of claim 1, wherein an exterior surface of the elongated hollow shaft includes a plurality of distance markings.

11. The method of claim 1, wherein the first attachment mechanism comprises an integral lock that is activated by a twisting motion between the first attachment mechanism and the second attachment mechanism.

12. The method of claim 1, wherein the first attachment mechanism includes a threaded component, and wherein a syringe is configured to be removably coupled to the first attachment mechanism via the threaded component.

13. The method of claim 1, wherein the first attachment mechanism includes a cavity including a pair of protrusions directed inward from the cavity, and wherein the second attachment mechanism includes a pair of flexible arms, and wherein the pair of flexible arms are configured to bend inward as the rod is moved distally within the lumen of the elongated hollow shaft and then snap around the pair of protrusions to thereby removably couple the first attachment mechanism to the second attachment mechanism.

14. The method of claim 1, wherein the second attachment mechanism includes a pair of protrusions directed outward, wherein the cap includes a pair of flexible arms including cutouts, and wherein the pair of flexible arms are configured to bend outward as the cap is moved distally with respect to the second attachment mechanism, and wherein the cutouts of the pair of flexible arms are configured to snap around the pair of protrusions to thereby removably couple the cap to the second attachment mechanism.

15. The method of claim 1, wherein the cap can be removed independently from the second attachment mechanism.

16. The method of claim 1, wherein the distal end of the elongated hollow shaft includes a plurality of side ports.

\* \* \* \* \*